(12) United States Patent
Segawa et al.

(10) Patent No.: US 8,091,164 B2
(45) Date of Patent: Jan. 10, 2012

(54) INTRODUCTION-ASSISTING APPARATUS FOR CAPSULE MEDICAL DEVICE

(75) Inventors: Hidetake Segawa, Hachioji (JP); Takeshi Yokoi, Hino (JP); Akira Kikuchi, Yokohama (JP); Hironobu Takizawa, Hachioji (JP); Akio Uchiyama, Yokohama (JP)

(73) Assignee: Olympus Corporation, Tokyo (JP)

( * ) Notice: Subject to any disclaimer, the term of this patent is extended or adjusted under 35 U.S.C. 154(b) by 1234 days.

(21) Appl. No.: 11/661,469

(22) PCT Filed: Dec. 28, 2004

(86) PCT No.: PCT/JP2004/019643
§ 371 (c)(1),
(2), (4) Date: Feb. 26, 2007

(87) PCT Pub. No.: WO2006/070472
PCT Pub. Date: Jul. 6, 2006

(65) Prior Publication Data
US 2007/0260175 A1    Nov. 8, 2007

(30) Foreign Application Priority Data

Oct. 6, 2003    (JP) ................................ 2003-347642
Oct. 7, 2003    (JP) ................................ 2003-348777

(51) Int. Cl.
*A61G 7/015* (2006.01)
*A61G 7/018* (2006.01)
*A61B 1/06* (2006.01)

(52) U.S. Cl. ..................... 5/613; 5/616; 5/617; 600/424

(58) Field of Classification Search ............... 5/613, 616, 5/617, 633, 634, 607, 942; 604/890.1, 891.1, 604/19, 131; 600/302, 424
See application file for complete search history.

(56) References Cited

U.S. PATENT DOCUMENTS

| 1,936,437 | A |   | 11/1933 | Peters |       |
|-----------|---|---|---------|--------|-------|
| 4,225,988 | A | * | 10/1980 | Cary et al. | 5/607 |
| 4,387,888 | A |   | 6/1983  | Marinakis |   |
| 5,479,665 | A | * | 1/1996  | Cassidy et al. | 5/613 |
| 5,537,701 | A | * | 7/1996  | Elliott | 5/617 |
| 5,604,531 | A |   | 2/1997  | Iddan et al. |   |

(Continued)

FOREIGN PATENT DOCUMENTS
CN    2416884 Y    1/2001
(Continued)

OTHER PUBLICATIONS

Japanese Office Action dated Oct. 6, 2009.
(Continued)

*Primary Examiner* — Robert G Santos
(74) *Attorney, Agent, or Firm* — Scully, Scott, Murphy & Presser, P.C.

(57) ABSTRACT

There is provided an assisting table capable of horizontally holding a subject and holding an angle at which a head of a subject is supported in an inclined state, and an assisting instrument, which includes a containing portion for containing a fluid to introduce a capsule medical device into a body cavity, capable of ejecting a capsule medical device with the fluid from the containing portion by detachably attaching the capsule medical device at a distal end opening portion of the containing portion and by changing a shape of the containing portion.

8 Claims, 14 Drawing Sheets

U.S. PATENT DOCUMENTS

| | | |
|---|---|---|
| 6,632,171 B2 | 10/2003 | Iddan et al. |
| 7,246,389 B2 * | 7/2007 | Taguchi et al. .................. 5/618 |
| 7,448,993 B2 * | 11/2008 | Yokoi et al. .................. 600/114 |
| 2003/0085994 A1 | 5/2003 | Fujita et al. |
| 2003/0167569 A1 | 9/2003 | Newkirk et al. |
| 2005/0085697 A1 * | 4/2005 | Yokoi et al. .................. 600/160 |
| 2005/0160530 A1 * | 7/2005 | Taguchi et al. .................. 5/618 |
| 2006/0085913 A1 * | 4/2006 | Kawakami et al. ................ 5/618 |
| 2007/0260175 A1 * | 11/2007 | Segawa et al. .................. 604/79 |

FOREIGN PATENT DOCUMENTS

| | | |
|---|---|---|
| CN | 2540844 Y | 3/2003 |
| JP | 63-65404 | 4/1988 |
| JP | 02-036848 | 2/1990 |
| JP | 02-182242 | 7/1990 |
| JP | 2-43382 | 11/1990 |
| JP | 03-111022 | 5/1991 |
| JP | 4-131214 | 12/1992 |
| JP | 06-269479 | 9/1994 |
| JP | 11-225996 | 8/1999 |
| JP | 2003-093332 | 4/2003 |
| JP | 2003-135389 | 5/2003 |
| JP | 2003-210395 | 7/2003 |
| JP | 2004-194976 | 7/2004 |
| JP | 2004-305505 | 11/2004 |
| WO | WO 01/35813 A1 | 5/2001 |

OTHER PUBLICATIONS

English Abstract only of CN 2416884 Y.
English Abstract only of CN 2540844 Y.
Supplementary Partial European Search Report dated Aug. 11, 2011 in counterpart European Patent Application No. EP 04807998.2.

* cited by examiner

INTRODUCTION-ASSISTING APPARATUS FOR CAPSULE MEDICAL DEVICE

TECHNICAL FIELD

The present invention relates to an introduction-assisting apparatus for capsule medical device, which is used for orally introducing into a body cavity a capsule medical device for an in-vivo inspection or the like.

BACKGROUND ART

In recent years, a capsule medical device has been widely used in a medical field. The capsule medical device is formed without an elongated insertion portion of an endoscope so that it is easier for a patient to swallow.

For example, Japanese Patent Laying-Open No. H2-36848 discloses, in FIG. 6, a view in which an inspection using a capsule medical device is performed in a state where a patient is lying face down.

In addition, U.S. Pat. No. 5,604,531 discloses, in FIG. 6, a view in which an inspection using a capsule medical device for vital observation is performed in a state where a patient is lying face up.

When a patient swallows the capsule medical device, the capsule medical device usually passes through an esophagus in several seconds, so that it has been difficult to perform a minute observation.

Therefore, in order to delay the passing speed of the capsule medical device, the patient usually stays lying down until the capsule passes through the esophagus.

In addition, the capsule medical device is usually swallowed with water to make it easier to pass through a pharynx.

However, as in the above-described prior example, it is a little difficult for a patient to swallow the capsule medical device and water while lying on a bed.

Furthermore, a capsule medical device of another prior example is, as recited, for example, in PCT publication No. WO 01/35813 A1, contained in a package in advance and used by taking out of the package immediately before use.

However, the above-described publication No. PCT WO 01/35813 A1 does not mention as to how the capsule medical device is introduced into a body cavity.

Normally, a subject firstly puts the capsule medical device in his or her mouth and introduces the capsule medical device into his or her body by swallowing the capsule medical device with water in a cup in a state where the upper half of the body is elevated, such as a standing state or a sitting state.

With the upper half of the body elevated, the capsule medical device introduced into the body quickly passes through lumens in the body cavity such as esophagus and stomach with the swallowed water, due to the effect of gravity. In this case, it is difficult to obtain an observation image and to sprinkle medication, and to perform therapeutic treatment and the like by making the capsule medical device slowly pass through the lumens in the body cavity by peristaltic motion. In addition, in regions such as a desert or dense forest and at the time of disasters such as an earthquake or fire, it is sometimes difficult to secure clean water for swallowing the capsule medical device.

Furthermore, it is a little difficult for a subject in a lying state to swallow a capsule medical device with water in a cup. In this case, the subject often has a difficulty in swallowing the capsule medical device with the water, because the subject sometimes spills water in cup or the water chokes the subject.

DISCLOSURE OF INVENTION

Means for Solving the Problem

Accordingly, a medical system is provided. The medical system comprising: a capsule medical device used for performing a medical practice including inspection and treatment, the capsule medical device being introduced into a body cavity; and an introduction-assisting apparatus for capsule medical device for supporting a subject when the capsule medical device is introduced into the body cavity, wherein the introduction-assisting apparatus for capsule medical device includes: a horizontally-holding device for generally horizontally holding an angle of an upper body except a cephalic part of the subject; and an inclination-holding device for holding an angle of the cephalic part in an upwardly inclined state relative to the upper body.

The introduction-assisting apparatus for capsule medical device can further comprise a lateral position-holding device for holding the upper body of the subject in a lateral position.

The inclination-holding device can be configured so that the inclination angle is adjustable. The inclination-holding device can be configured so that the inclination angle is adjustable by a pressing operation. The inclination-holding device can comprise: a motor for adjusting the inclination angle; and a switch for supplying drive current to the motor.

The inclination-holding device can be detachably attached to the horizontally-holding device.

The capsule medical device can be attached with a string member by an adhesive of which fixing is released at a predetermined time period. The adhesive can be water-soluble.

Also provided is a medical system. The medical system comprising: a capsule medical device used for performing a medical practice including inspection and treatment, the capsule medical device being introduced into a body cavity; and an introduction-assisting apparatus for capsule medical device for supporting a subject when the capsule medical device is introduced into the body cavity, wherein the introduction-assisting apparatus for capsule medical device includes: a horizontally-holding device for generally horizontally holding an angle of an upper body except a cephalic part of the subject; and an opening portion formed near a position with which the cephalic part of the subject comes into contact, the opening portion being provided to the horizontally-holding device.

A rack can be provided under the opening portion.

Still yet provided is an inspection method for capsule medical device for inspecting inside a body by introducing a capsule medical device from an oral cavity of a subject. The method comprising the steps of: horizontally holding an upper body of the subject and obliquely upwardly inclining a cephalic part thereof; introducing the capsule medical device into the subject from an oral cavity; and horizontally holding the cephalic part of the subject.

Still yet further provided is a medical system. The medical system comprising: a capsule medical device used for performing a medical practice including inspection and treatment, the capsule medical device being introduced into a body cavity; and an introduction-assisting apparatus for assisting introduction of the capsule medical device into the body cavity, wherein the introduction-assisting apparatus for capsule medical device includes a containing portion for containing a fluid used to introduce the capsule medical device into a body.

The containing portion can be a flexible member capable of changing a volume capacity thereof.

The containing portion can be a syringe capable of changing a volume capacity thereof.

The fluid contained in the containing portion can be at least one of a liquid, a gas and a gelatinous material.

The medical system can comprise a package for sealing the introduction-assisting apparatus for capsule medical device in a sterilized state. The introduction-assisting apparatus for capsule medical device can be sealed in the package in a state where the fluid is contained in the containing portion.

The introduction-assisting apparatus for capsule medical device can comprise: an opening portion which is provided to the containing portion and communicates with the containing portion; and a mounting portion in which the capsule medical device is attached to the opening portion, wherein the capsule medical device is introduced into the body cavity along with a fluid that flows and moves from the containing portion to the mounting portion by a change of volume capacity of the containing portion. The mounting portion can be formed of a flexible member. The mounting portion can be detachably attached to the opening portion; the opening portion can be thinly formed and include a sealing portion for sealing the containing portion; the mounting portion can include a projection portion; and the projection portion can perforate the sealing portion when connecting the mounting portion attached with the capsule medical device to the opening portion.

The capsule medical device can comprise: a load portion for performing a medical practice including inspection and treatment; a power source for supplying electric power to the load portion; and a switch for supplying and shutting off the power source to the load portion, wherein the introduction-assisting apparatus for capsule medical device can include a switch control portion for controlling the switch. The switch control portion can be equipped to the mounting portion. The switch can be a magnetic switch, and the switch control portion can be a magnet.

An intracavital introduction portion for introducing the capsule medical device into a body cavity can be provided between the opening portion and the mounting portion. The intracavital introduction portion can be formed of a flexible member.

The medical system can comprise a package for sealing in a sterilized state the introduction-assisting apparatus for capsule medical device in a state where the containing portion contains the fluid and the capsule medical device is attached to the mounting portion.

Further yet provided is an inspection method for capsule medical device for inspecting inside a body by introducing a capsule medical device from an oral cavity of a subject. The method comprising the steps of horizontally holding an upper body of the subject; inserting the capsule medical device into an oral cavity of the subject; restricting a position of the capsule medical device to near a pharynx of the subject; and introducing the capsule medical device.

The inspection method can further comprise, after the step of horizontally holding the upper body of the subject, a step of obliquely upwardly inclining a cephalic part of the subject. The inspection method can further comprise, after the step of introducing the capsule medical device, a step of horizontally holding the cephalic part of the subject.

BEST MODE FOR CARRYING OUT THE INVENTION

Hereinafter, each embodiment of the present invention will be described with reference to the drawings.

First Embodiment

Figure 1:
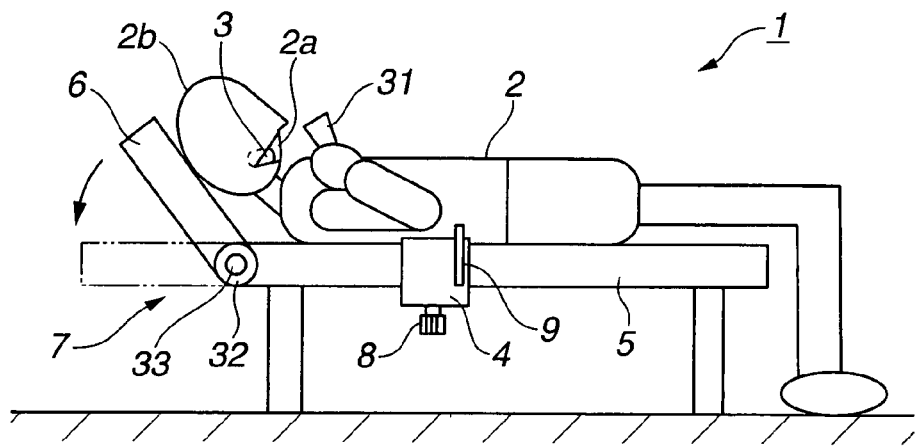
FIG. 1 is an overall configuration view of a medical system applied with a first embodiment of the present invention.
Figure 2:
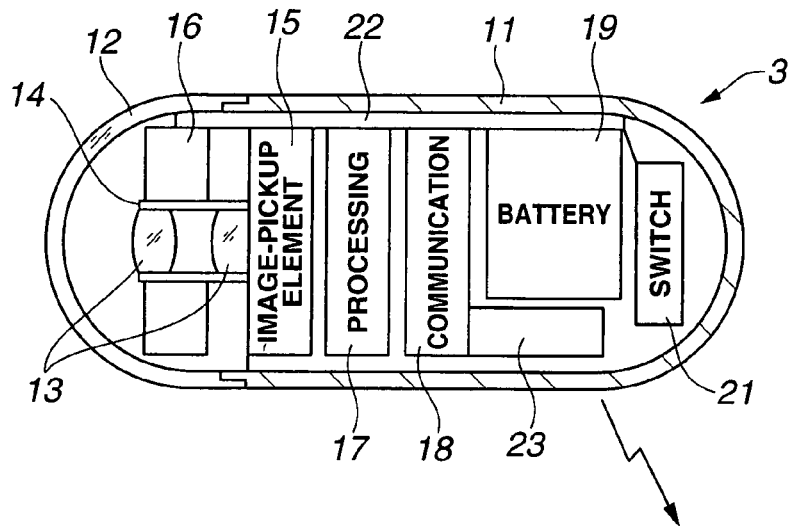
FIG. 2 is a view showing configurations of a capsule medical device and an extracorporeal unit.
Figure 2:
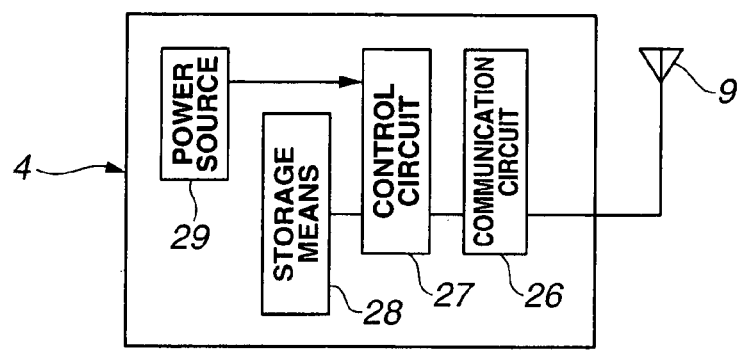
Figure 3:
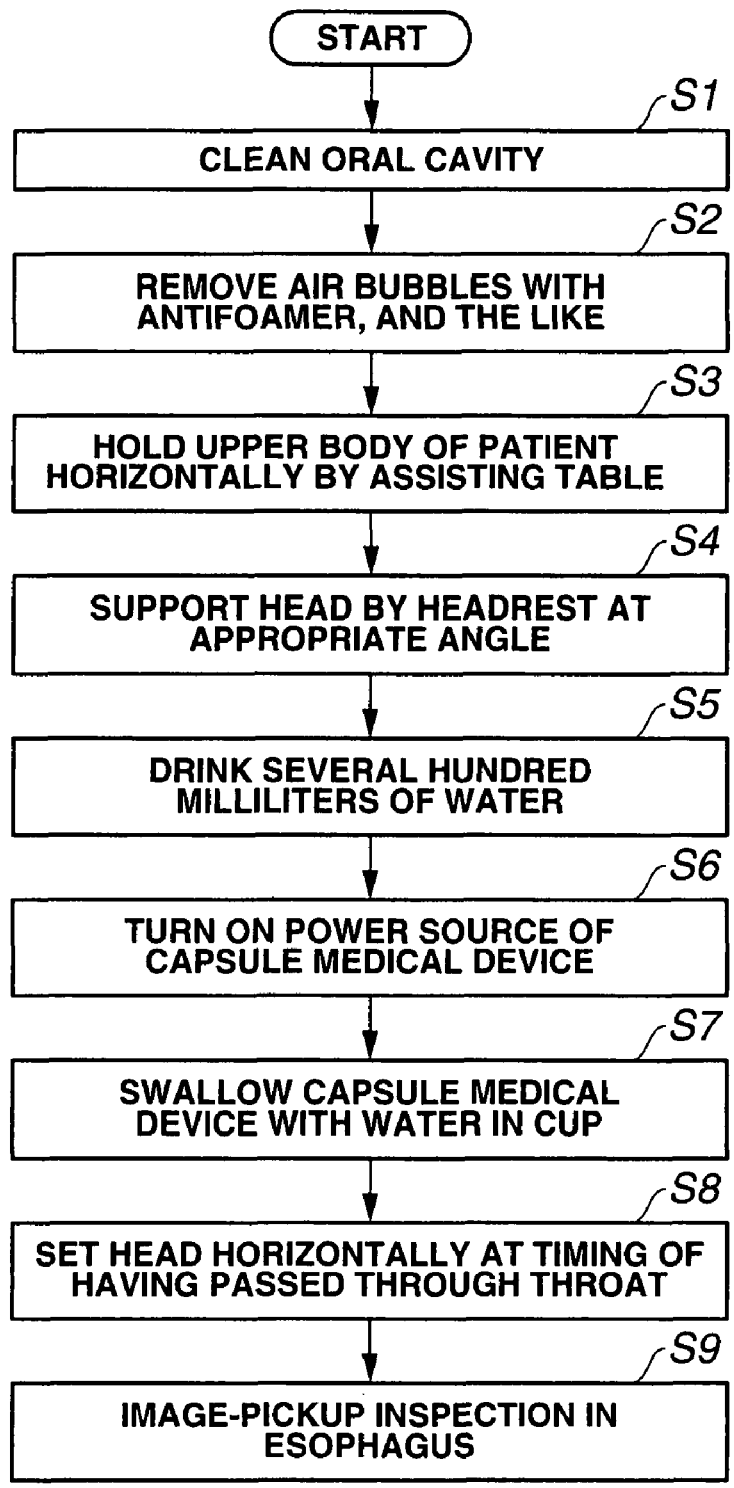
FIG. 3 is a flowchart showing processes of an inspection method.

FIGS. 1 to 3 are related to a first embodiment of the present invention. FIG. 1 shows an overall configuration of a medical system applied with the first embodiment of the present invention as an example of use, FIG. 2 shows configurations of a capsule medical device and an extracorporeal unit, and FIG. 3 shows processes of an inspection method. Hereinafter, description will be made on an introduction-assisting apparatus (abbreviated simply as an assisting apparatus) for a capsule medical device and a medical system provided with the assisting apparatus. The assisting apparatus is used, when an inspection is performed in an upper gastrointestinal tract of a subject, specifically in esophagus with a capsule medical device, for obtaining minute inspection information by slowing down a passing speed through the site.

As shown in FIG. 1, a medical system 1 applied with the first embodiment includes a capsule medical device 3 for inspecting a body cavity of a patient 2 as a subject, an extracorporeal unit 4 for receiving and accumulating biological information transmitted by the capsule medical device 3, and an assisting table 7 provided with, for example, a base member 5 and a headrest 6 as an introduction-assisting apparatus (inspection-assisting apparatus) for assisting to introduce the capsule medical device 3 or to perform an inspection using the same.

The bed-like base member 5 constituting the assisting table 7 has a function as horizontally-holding means for horizontally holding the upper half of the body (upper body) of the patient 2. In addition, the headrest 6 has a function as inclination-holding means for supporting a head 2b of the patient 2 with the head being inclined upwardly from a horizontal direction, and this function enables the patient 2 to easily swallow the capsule medical device 3 with water.

As shown in FIG. 2, the capsule medical device 3 includes an exterior member main body 11 of cylindrical shape having one end portion semispherically closed and a transparent cover 12 of semispherical shape fitted and fixed to an opening of the other end portion of the exterior member main body 11, thus forming an exterior container of which inner portion has a watertight structure.

At the center portion of inner side of the transparent cover 12 inside the exterior container, an object lens 13 for forming an optical image of an object to be observed is disposed being attached to a lens frame 14, and at an image-forming position of the object lens 13, an image-pickup element 15 for picking up images, such as a CMOS imager and the like, is disposed.

Furthermore, around the object lens 13, a plurality of white LEDs 16, for example, are disposed as an illuminating device.

On the rear side of the image-pickup element 15, disposed are a processing circuit 17 for driving the white LEDs 16 as well as driving the image-pickup element 15 and performing signal processing and the like, a communication circuit 18 for transmitting to the extracorporeal unit 4 a signal of the image picked up by the image-pickup element 15, a battery 19 for supplying operating power to each circuit or the like, and a switch 21 for turning on and off the battery 19.

Furthermore, in the longitudinal direction of the exterior member main body 11, disposed is a flexible printed circuit (abbreviated as FPC) 22. The FPC 22 is electrically connected to the image-pickup element 15, the processing circuit 17, the communication circuit 18, the battery 19, and the switch 21.

In addition, to the communication circuit 18, connected is an antenna 23 for transmitting a signal by wireless to the extracorporeal unit 4.

Furthermore, as shown in FIG. 1, the extracorporeal unit 4, which receives biological information from the capsule medical device 3, has a box shape, for example, and includes an attaching portion 8 that is detachably attachable to the base member 5. Also, the extracorporeal unit includes an antenna 9, extended outwards therefrom, for receiving the biological information transmitted through radio waves from the antenna 23 of the capsule medical device 3.

As shown in FIG. 2, the extracorporeal unit 4 includes a communication circuit 26 for performing demodulation or the like to the signals received by the antenna 9 extended outwards from the unit, a (processing and) control circuit 27 for converting the signal demodulated by the communication circuit 26 into a digital signal to perform compression processing and the like to the digital signal and for performing control operation, storage means 28 constituted of a nonvolatile memory such as EEPROM, etc., connected to the control circuit 27, and a power source 29, such as a battery, for supplying operating power to the control circuit 27, and the like.

When swallowing the capsule medical device 3, the patient 2 uses the assisting table 7 as shown in FIG. 1 and puts the capsule medical device 3 in an oral cavity 2a, then drinks the water in a cup 31 together in order to make the capsule medical device 3 smoothly pass through the pharynx. Thus, it is possible to perform an inspection in the body cavity such as esophagus.

In this case, the upper side (upper half of the body) of the patient 2 is held horizontally on a horizontal surface formed with the bed-like base member 5. To one end in the longitudinal direction of the base member 5, attached is a headrest 6, of which tilting angle can be freely changed by a pivotally supporting portion 32, for supporting the head (cephalic part) 2b at an appropriate inclined angle. As shown in FIG. 1, the headrest 6 enables the inclined angle supporting the head 2b of the patient 2 to be set at 60 to 90 degrees from the horizontal surface of the base member 5.

In the present embodiment, as shown in FIG. 1, since the angle of the upper body of the patient 2 other than the head 2b is held generally horizontally by the base member 5 of the assisting table 7, and the angle of the head 2b is held by the headrest 6 in an upwardly inclined state relative to the upper body, it is easy to swallow the capsule medical device 3. In addition, holding the upper body horizontally by the base 5 slows down the moving speed of the swallowed capsule medical device 3, thus allowing for minute inspection and the like.

In the present embodiment, the pivotally supporting portion 32 is further provided with an adjusting screw (a knob thereof) 33 for adjusting an amount of force to rotatably support the headrest. When the head 2b is pressed against the side of the headrest 6 with the headrest being set at an appropriate inclined angle, the headset 6 is rotated in a direction in which the inclined angle thereof becomes smaller as shown by an arrow, due to rotation of the pivotally supporting portion 32, and as a result, the headrest 6 can be set generally horizontally as shown by a dashed two-dotted line.

As described below, immediately after the patient swallowed the capsule medical device 3, the head 2b as well as the headrest 6 are set in a generally horizontal state, and the moving speed of the capsule medical device is set slow immediately after the swallowing. Accordingly, it is possible to perform a minute inspection from near the position where the device is located immediately after the swallowing.

Next, description will be made on an action that the patient 2 swallows the capsule medical device 3 and an inspection in the body cavity is performed with the capsule medical device 3, based on an inspection method shown in FIG. 3.

The inspection processes by swallowing the capsule medical device 3 are as follows.

At first, as shown in Step S1, cleaning in an oral cavity 2a is performed to remove saliva and control saliva production.

As the cleaning method in the oral cavity 2a, there are such methods as gargle with cleaning solution such as popidone-iodine solution, domiphen bromide, sodium azulene sulfonate, sodium bicarbonate water, hydrogen peroxide, benzethonium chloride, and the like, brushing with a toothbrush, and high-pressure water jetting by a water pick.

In the next Step S2, the patient 2 takes an antifoamer, such as dimethicone and dimethylpolysiloxane, to remove air bubbles in a gastrointestinal tract.

Moreover, immediately before swallowing the capsule medical device 3, the patient drinks several hundred milliliters of water to remove newly produced or remained saliva and air bubbles.

After that, the patient 2 lies on the bed-like base member 5 shown in FIG. 1 to swallow the capsule medical device 3 with water.

In this case, as shown in Step S3, the upper half of the body of the patient 2 is horizontally held by the assisting table 7 (the base member 5 thereof). Furthermore, as shown in Step S4, the head 2b of the patient 2 is supported at an appropriate angle, that is, in a state where the head 2b is raised from the horizontal direction.

As described above, the patient 2 or the like sets the headrest 6 at an appropriate angle relative to the base member 5, for example, in a state of being raised at 60 to 90 degrees, to support the head 2b by the headrest 6. In this state, the head 2b side is positioned more upward than the cervix side. Furthermore, as shown in Step S5, immediately before swallowing the capsule medical device 3, the patient drinks several hundred milliliters of water to remove the newly produced or remained air bubbles.

After that, as shown in Step S6, the patient 2 operates the switch 21 of the capsule medical device 3 to turn on the power.

Then, as shown in Step S7, the patient puts the capsule medical device 3 in the oral cavity 2a, and holding the cup 31 containing water in his or her hand, pours into the oral cavity 2a the water in the cup 31 to swallow the capsule medical device 3 with the water.

Then, as shown in Step S8, at an appropriate timing immediately after the capsule medical device 3 has passed through the throat, the patient 2 presses the head 2b against the headrest 6 to rotate the headrest 6 by the pivotally supporting portion 32 and set the head 2b also in a horizontal state as the upper half of the body.

Accordingly, since the upper part of the esophagus of the patient 2 is promptly set generally horizontal after the swallowing, the moving speed of the swallowed capsule medical device 3 in the upper part of the esophagus can be slowed down, so that images can be picked up multiple times per unit time when the capsule medical device 3 moves from the upper part to the middle and lower parts of the esophagus. As a result, minute inspection can be performed.

Therefore, it is possible to acquire the images obtained by minutely picking up the inside of the esophagus from immediately after the swallowing, and this is greatly effective for the minute diagnosis.

Thus, according to the present embodiment, when swallowing the capsule medical device 3, the patient sets the head 2b at an appropriate angle rising up from the horizontal direction using the headrest 6, so that the patient can swallow the capsule medical device in an easier state for swallowing. Then, the patient quickly sets the head 2b in a generally horizontal state by pressing the head 2b against the headrest 6 immediately after the swallowing, so that the moving speed of the capsule medical device 3 from the upper part of the esophagus is slowed down, and thus a minute inspection can be performed.

Second Embodiment

Figure 4A:
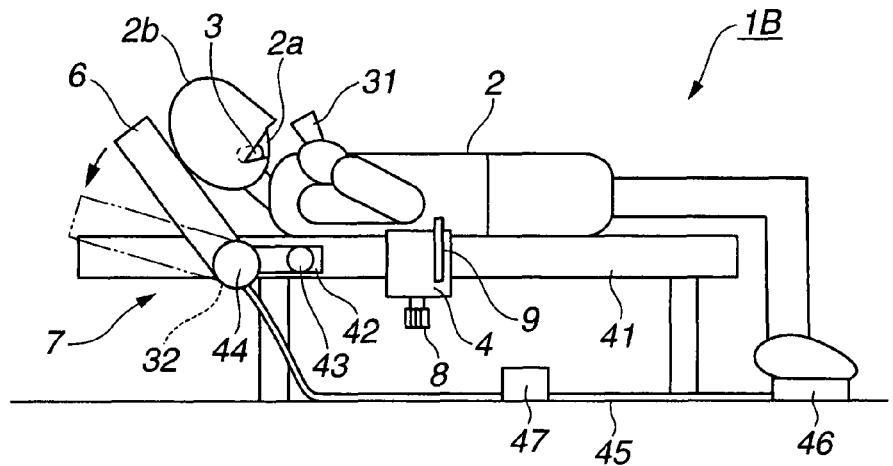
FIG. 4A is a side view showing an overall configuration of a medical system applied with a second embodiment of the present invention.
Figure 4B:
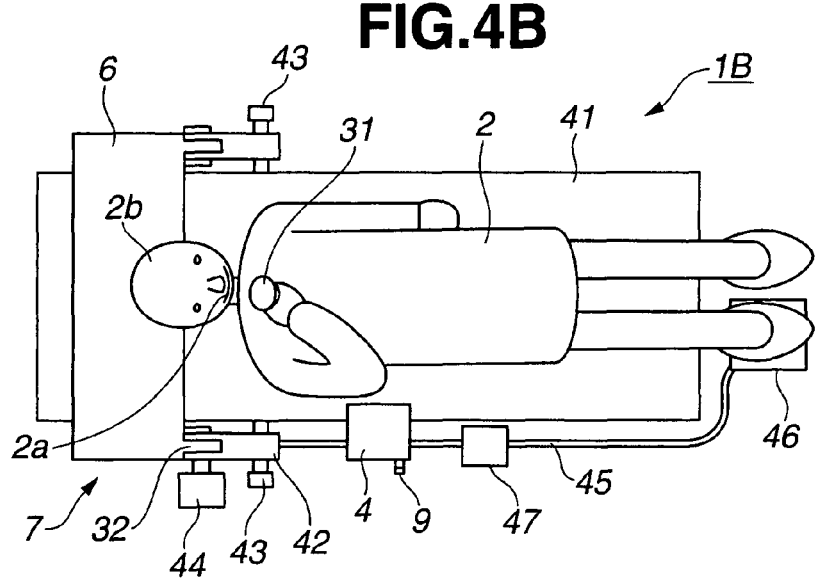
FIG. 4B is a plan view showing an overall configuration of a medical system according to the second embodiment of the present invention.

Next, a second embodiment of the present invention will be described with reference to FIGS. 4A and 4B. Note that FIGS. 4A and 4B are side view and plan view of a medical system 1B, respectively. The present embodiment improves an operability compared with the first embodiment.

In the medical system 1B applied with the present embodiment, an assisting table 7 is formed by being provided with an attaching member 42 for detachably attaching a headrest 6 to a bed 41 in the medical system 1 shown in FIG. 1, instead of the headrest 6 integrally provided to the base member 5.

The attaching member 42 is provided with fixing screws 43, so that the attaching member 42 can be detachably fixed on both sides of the bed 41. In addition, a motor 44 is attached to a pivotally supporting portion 32 for rotatably holding the headrest 6, and rotational driving of the motor 44 causes the headrest 6 to recline to near the position shown by a dashed two-dotted line in FIG. 4A.

The motor 44 is connected to a foot switch 46 via a cable 45. The patient 2 steps on the foot switch 46 so as to supply driving power from a battery in a battery box 47 to the motor 44 to rotate the motor 44, thus enabling the headrest 6 to recline. This realizes approximately the same function as in the first embodiment while further improving operability.

Other configurations are the same as those of the first embodiment. Next, an operation of the present embodiment will be described.

In the first embodiment, in a case of swallowing the capsule medical device 3 with the water in the cup 31, the patient 2 presses the head 2b against the side of the headrest 6 to recline the headrest 6, and quickly sets the cervix as well as the head 2b in the generally horizontal state, thus making the swallowed capsule move slowly.

On the contrary, in the present embodiment, the patient 2 steps on the foot switch 46 to rotationally drive the motor 44 immediately after swallowing the capsule medical device 3 with the water in the cup 31.

Due to the rotation of the motor 44, also the head 2b supported by the headrest 6 becomes the generally horizontal state with the reclining of the headrest 6 in the horizontal direction. Therefore, the capsule medical device 3 which has passed through the throat of the patient 2 is promptly set in a state where the moving speed thereof is slowed down.

Thus, according to the present embodiment, almost the same effect as that in the first embodiment can be obtained while improving the operability. Furthermore, in the present embodiment, since the assisting table 7 can be formed by utilizing the existing bed 41 to which the attaching member 42 for detachably attaching the headrest 6 is provided. Therefore, a user can realize the medical system 1B with reduced economic burden.

Figure 5:
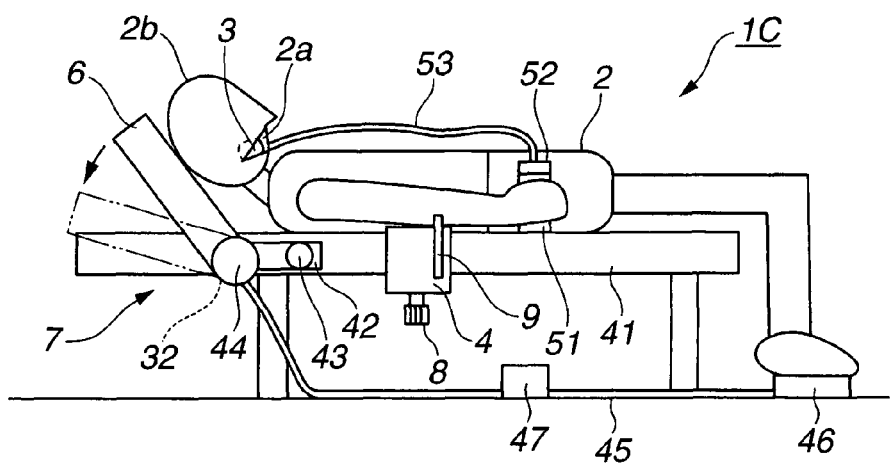
FIG. 5 is an overall configuration view of a medical system of a modified example.

FIG. 5 shows a configuration of a medical system 1C as a modified example with an example of use. In the modified example, instead of using the cup 31 in FIG. 4, a flexible bottle 51 containing water is used. The bottle 51 has an opening upper end closed with a cap 52 from which a flexible tube 53 integrally provided to the cap is extended, for example. Then, the patient 2 holds the bottle 51 in his or her hand and applies pressure so as to deflate the bottle 51. As a result, the water inside the bottle runs through the tube 53 and spouts from the distal end thereof.

Accordingly, when swallowing the capsule medical device 3 with water, as shown in FIG. 5, the patient 2 has only to put the capsule medical device 3 into the oral cavity 2a and put the distal end of the tube 53 in the oral cavity 2a to deflate the bottle 51.

According to the present modified example, almost the same effect as that of the second embodiment can be obtained, while surely preventing the water from spilling compared with the configuration in which the cup 31 is used.

Third Embodiment

Figure 6:
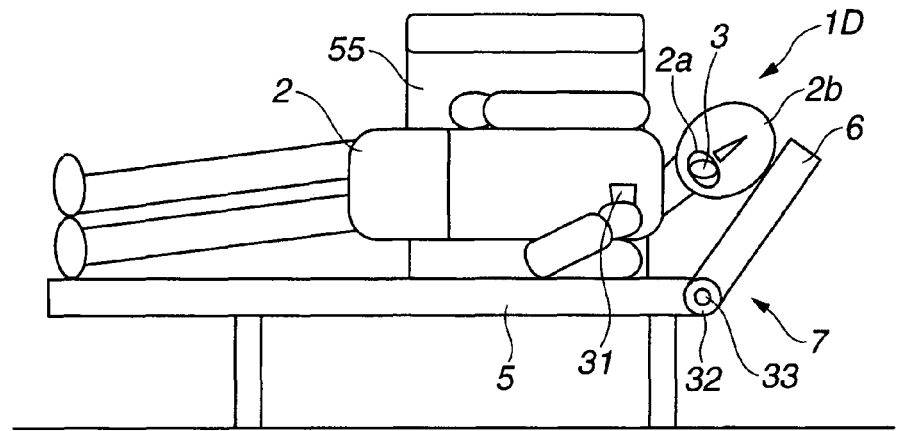
FIG. 6 is a side view of a medical system according to a third embodiment of the present invention.
Figure 7:
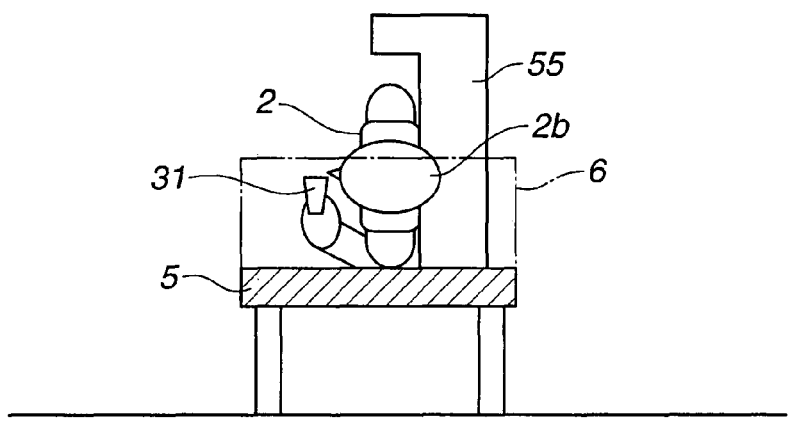
FIG. 7 is a front view of the medical system.

Next, a medical system 1D applied with a third embodiment of the present invention will be described with reference to FIGS. 6 and 7. FIG. 6 is a side view of a medical system 1D applied with the third embodiment seen from a side direction, and FIG. 7 is a front view of the main part of FIG. 6. Note that, in the present embodiment, description will be made omitting the extracorporeal unit 4.

The medical system 1D is provided with, in addition to the assisting table 7 in the medical system 1 in FIG. 1, a backrest 55 for supporting the rear side of a patient 2. The backrest 55 is fixed generally vertically relative to a base member 5.

In the present embodiment, before swallowing a capsule medical device 3, the patient 2 lies on the assisting table 7 in the lateral position to laterally support the head 2b by a headrest 6. In the state, the patient 2 can keep generally vertically the head 2b while keeping horizontally the upper body from the neck down, so that the patient can easily swallow the capsule medical device 3 with water. In addition, the rear side of the patient 2 in the lateral position, that is the back of the patient, is supported by the backrest 55.

The present embodiment is capable of reducing or extending the retention time period of the capsule medical device 3 in the stomach, in addition to achieving the effect of the first embodiment.

For example, when the patient 2 is in the left lateral position, the pylorus of the stomach is positioned on the upper side, so that the retention time period of the capsule medical device in the stomach is extended compared with a case where the patient is in an upright position.

On the other hand, when the patient is in the right lateral position, the pylorus of the stomach is positioned on the lower side, so that it is possible to reduce the time period until the capsule is discharged from the stomach.

Fourth Embodiment

Figure 8:
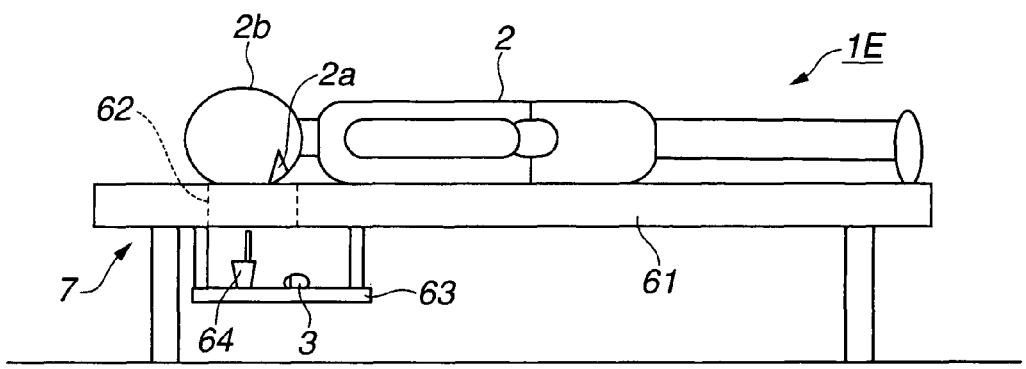
FIG. 8 is a side view of a medical system according to a fourth embodiment of the present invention.
Figure 9:
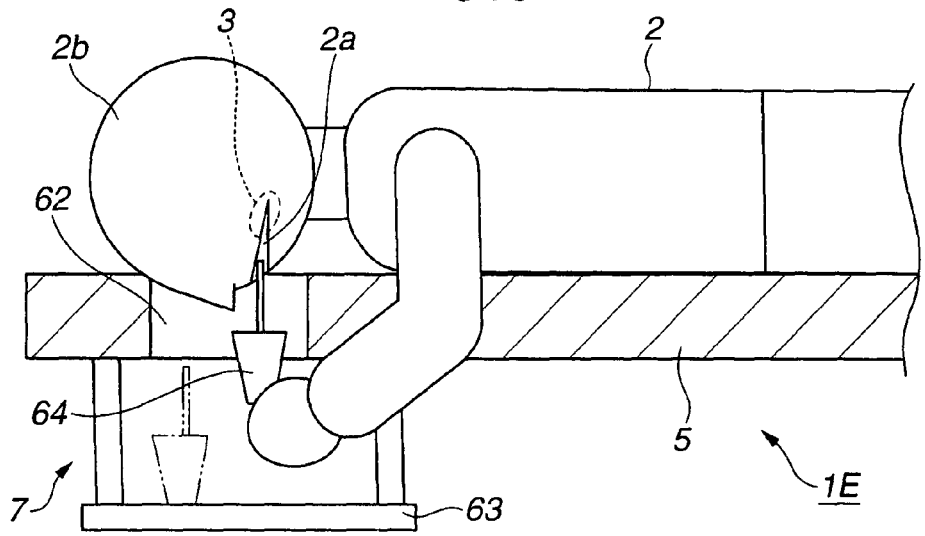
FIG. 9 is a cross-sectional view showing a main part of FIG. 8 in an enlarged manner.

Next, a medical system 1E according to a fourth embodiment of the present invention will be described with reference to FIGS. 8 and 9. FIG. 8 is a side view of the medical system 1E applied with the fourth embodiment seen from a side direction, and FIG. 9 illustrates a cross section of the main part of FIG. 8 in an enlarged manner.

As shown in FIG. 8, in the present embodiment, an assisting table 7 is formed by being provided with a through-hole 62 in a vertical direction near one end of a horizontal base 61. The size of the through-hole 62 is smaller than that of the head 2b of the patient 2, and the through-hole is an opening having a size to cover the mouth, nose, and eyes of the patient.

Under the through-hole 62, a rack portion of a tray 63 is horizontally attached so that upper ends of supporting rods are suspended at the bottom face of the base 61. The size of the rack of the tray 63 is large enough to place a straw bottle 64 containing water and a capsule medical device 3, and the height thereof is set within the reach of the hand of the patient 2 when the patient lies face down on the base 61.

Before swallowing the capsule medical device 3, the patient 2 lies face down on the assisting table 7, with the mouth, nose, and eyes facing with the through-hole 62. At this time, the straw bottle 64 containing water and the capsule medical device 3 are placed on the rack portion of the tray 63.

After that, as the main part is shown in FIG. 9 in an enlarged manner, the patient 2 puts the capsule medical device 3 in an oral cavity 2a and drink the water in the straw bottle 64. Accordingly, the patient can easily swallow the capsule medical device 3, while keeping the upper body horizontal.

According to the present embodiment, the patient 2 can swallow the capsule medical device 3 with water, while keeping the head 2b generally in parallel likewise with the state of the upper body. Therefore, the patient is not required to move the head 2b in the horizontal direction after the swallowing, and a minute inspection can be performed from the upper side of the esophagus.

Figure 10:
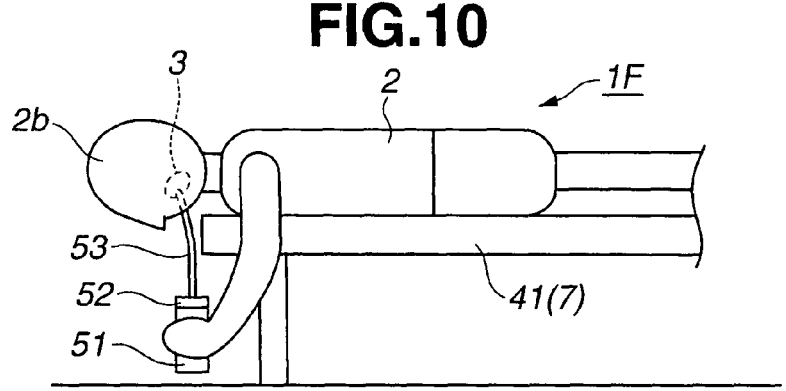
FIG. 10 is a side view of a medical system of a modified example.

FIG. 10 shows a main part of a medical system 1F applied with a modified example. In the modified example, a bed 41 is used as the assisting table 7. When the patient 2 puts his or her upper body on the bed 41 and lies face down, the patient lies face down on the bed 41 so that the vicinity of the head 2b protrudes from one end of the bed 41.

When swallowing the capsule medical device 3 with water, as shown in FIG. 10, the patient 2 puts the capsule medical device 3 in the oral cavity and may drink water using the bottle 51 described in FIG. 5, for example.

The modified example enables the patient to easily swallow the capsule medical device 3 with a simple configuration, while allowing for a minute inspection from the upper side of the esophagus.

Fifth Embodiment

Next, a medical system 1G applied with a fifth embodiment of the present invention will be described with reference to FIGS. 11 and 12.

Figure 11:
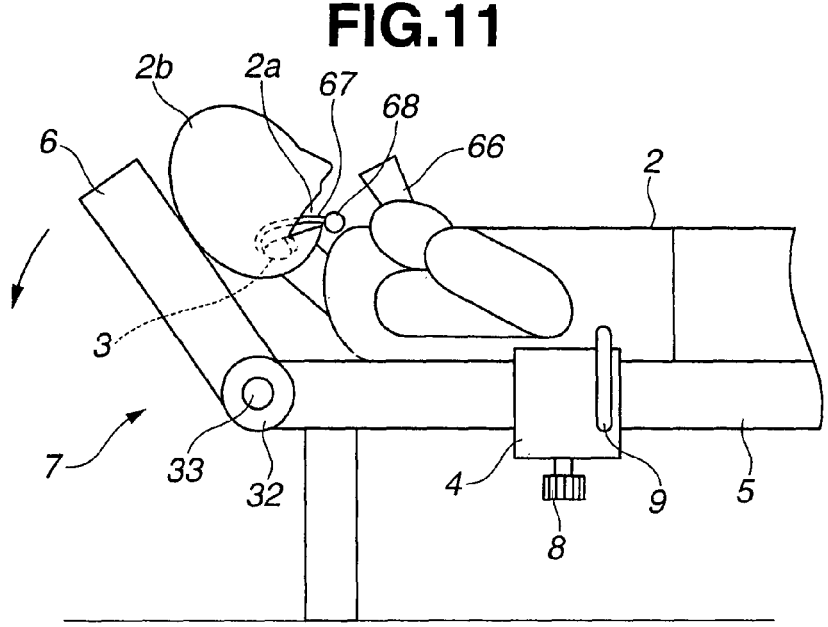
FIG. 11 is a side view of a medical system according to a fifth embodiment of the present invention.

The medical system 1G applied with the present embodiment shown in FIG. 11 includes the capsule medical device 3 further provided with a string member 66 in the medical system 1 shown in FIG. 1, for example.

Figure 12:
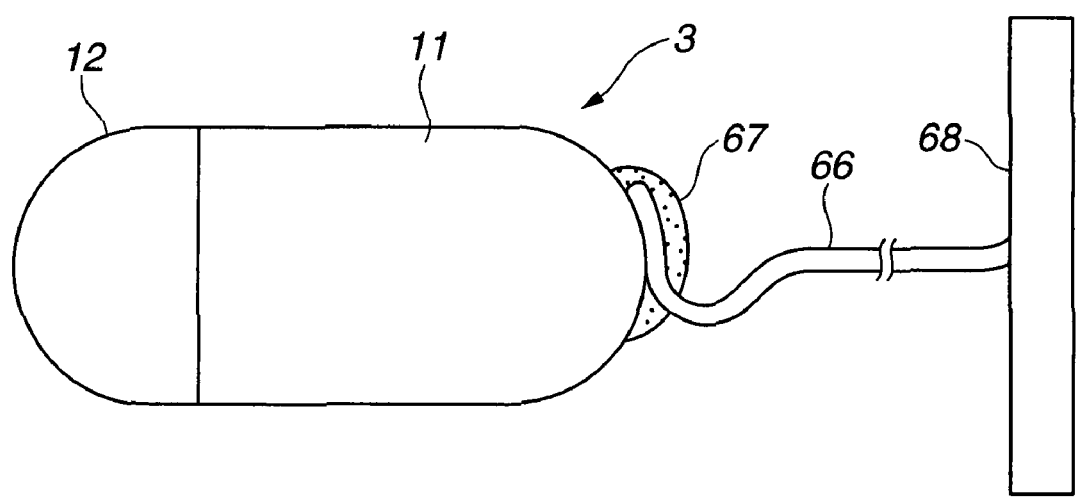
FIG. 12 is a side view showing a capsule medical device.

FIG. 12 shows the capsule medical device 3 to which the string member 66 is attached. To the rear end of the exterior member main body 11 of the capsule medical device 3, which is the opposite side of the transparent cover 12, one end of the string member 66 having flexibility is attached with a water-soluble adhesive 67, for example. In addition, the other end of the string member 66 is fixed to, for example, a bar-like member 68 to prevent the string member from being swallowed into the oral cavity 2a.

In this case, since the string member 66 is attached to the exterior member main body 11 of the capsule medical device 3 with the adhesive 67 which is water-soluble and safe for eating and drinking such as candy, for example, the adhesive dissolves in about several tens of seconds after the insertion of the capsule medical device in the oral cavity 2a, so that the string member 66 and the capsule medical device 3 are separated. That is, to the capsule medical device 3, the string member 66 of which fixing is released within a range of a short predetermined time period is attached.

Furthermore, the length of the string member 66 is set to be the same as the length from the entrance of the oral cavity 2a (that is, the mouth) to near the position immediately after passing through the throat.

Therefore, as shown in FIG. 11, the patient puts the capsule medical device 3 in the oral cavity 2a and drinks the water in a cup 31, so that the patient can swallow the capsule medical device 3 with the water. The swallowed capsule medical device 3 is retained near the position passing through the throat by the string member 66. Then, the adhesive 67 dissolves in several to several tens of seconds, and the capsule medical device 3 is separated from the string member 66.

Before the separation is completed, the patient 2 has only to move the head 2b to be in a horizontal state by reclining the headrest 6 and the like.

The present embodiment does not require the action to make the head 2b horizontal at a short timing immediately after swallowing the capsule medical device 3. Therefore, even if the timing is delayed, the moving speed of the swallowed capsule medical device 3 can be slowed down, so that a minute inspection from the upper side of the esophagus is possible.

Furthermore, in the present embodiment, the patient 2 swallows the capsule medical device 3 to which the string member 66 is connected, it is easier for the patient to set the side of the transparent cover 12 as the distal end when swallowing the capsule medical device.

Note that, instead of the adhesive 67 soluble in water in several to several tens of seconds, the string member 66 may be glued with low adhesive strength such that the fixing of the string member 66 can be released by applying pulling force thereto.

Note that, in the description above, as the capsule medical device 3, description was made on the configuration in which inspection and diagnosis are performed by optically picking up the images in a body cavity. However, the present invention is not limited to the configuration, but the capsule medical device may be, for example, configured so as to include a medicinal solution containing portion for storing a medicinal solution and perform medical treatment (medical action) by sprinkling the medicinal solution at a site to be treated such as esophagus and others.

Sixth Embodiment

Next, a sixth embodiment of the present invention will be described with reference to FIGS. 13 to 17. In the above-described first to fifth embodiments, descriptions were made mainly on the assisting table. However, in the present embodiment and thereafter, descriptions will be made mainly on an introduction-assisting instrument as an introduction-assisting apparatus for smoothly introducing a capsule medical device into a body cavity by swallowing.

The object of the following embodiments is to provide an introduction-assisting apparatus for capsule medical device for allowing a subject to swallow the capsule easily even in a lying state, while unifying conditions for swallowing the capsule medical device (fluid amount, and the like).

Figure 13:
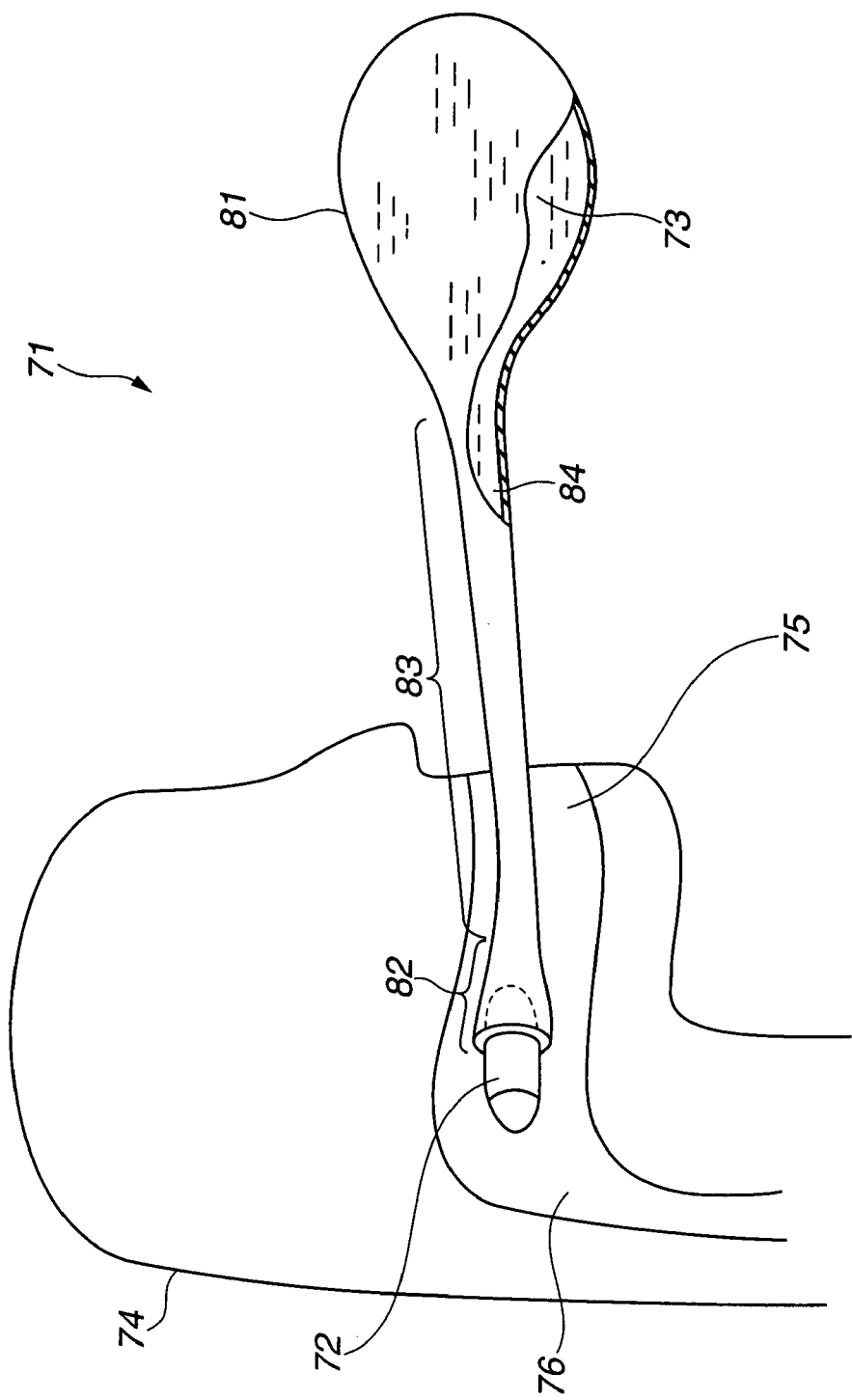
FIG. 13 is a view showing an introduction-assisting instrument according to a sixth embodiment of the present invention in a using state.

As shown in FIG. 13, an introduction-assisting instrument 71 as the sixth embodiment of the introduction-assisting apparatus for capsule medical device of the present invention is an assisting instrument for introducing a capsule medical device 72 into a body cavity of a subject 74 in a state where the subject 74 is lying. Note that, also in this case, the use of the above-described assisting table 7 enables a more appropriate inspection to be performed.

The above-described capsule medical device 72 is swallowed from an oral cavity 75 of the subject to pass through a tract in the body cavity, and obtains image data by, for example, optically picking up inner wall surface of the tract in the body cavity. Note that, the capsule medical device 3 shown in FIG. 2 may be used as the capsule medical device 72. Furthermore, though not shown in the present embodiment, the capsule medical device 72 may communicate wirelessly with the extracorporeal unit 4 to obtain image data, as shown in FIG. 2.

Note that, as for the capsule medical device 72, it may be configured such that the image data is obtained by retrieving the capsule medical device 72 from the body cavity instead of wirelessly communicating with the extracorporeal unit 4.

The above-described introduction-assisting instrument 71 includes a pouch-shaped containing portion 81 containing a fluid 73 for introducing the capsule medical device 72 into a body cavity by swallowing, and a mounting portion 82 for enabling the capsule medical device 72 to eject together with the fluid 73 contained in the containing portion 81, by detachably mounting the capsule medical device 72 to a distal end opening portion of the containing portion 81 and performing the operation of changing at least containing volume capacity of the containing portion 81.

That is, by mounting the capsule medical device 72 to the distal end opening portion of the flexible and deformable pouch-shaped containing portion 81 which contains the fluid 73 and performing the operation to change the containing volume capacity of the containing portion 81 by deflating the containing portion 81 and the like, the introduction-assisting instrument 71 is capable of ejecting or spouting the capsule medical device 72 mounted to the opening portion together with the fluid 73.

The introduction-assisting instrument 71 includes, between the containing portion 81 provided on the rear end side thereof and the mounting portion 82 provided on the distal end side thereof, a hollow and tubular intraoral introduction portion 83 which is formed in a tube shape so as to introduce the mounting portion 82 into an oral cavity 75 and has a flow path 84 formed therein through which the fluid 73 passes.

The containing portion 81 is formed in a pouch shape with an elastic member such as rubber, and capable of containing the fluid 73 inside thereof by predetermined amount, approximately 30 to 50 cc, while keeping a liquid-tight or air-tight state to prevent the fluid 73 from leaking. The fluid 73 to be contained in the containing portion 81 includes liquid such as so-called Gascon water (liquid containing antifoaming agent) having effects of removing mucus and antifoaming, and mineral water, gas such as air, gelatinous material such as jelly, and the like.

The containing portion 81 is thickly formed with the elastic member so that, by crushing (compressing) the rear end side, the fluid 73 contained therein flows (moves) to the side of the cylindrical-shaped mounting portion 82 with an opening and a predetermined power is generated in a direction to push forward and eject the capsule medical device 72 detachably mounted to the mounting portion 82.

The mounting portion 82 is thickly formed with the elastic member so as not to deform, and the distal end portion thereof is more thickly formed. The distal end portion of the mounting portion 82, into which the capsule medical device 72 can be easily fitted, has a predetermined holding power for holding the fitted capsule medical device 72 to prevent the fluid 73 contained in the containing portion 81 from leaking.

Into the mounting portion 82, the fluid 73 flows (moves) from the containing portion 81, and the power transmitted from the containing portion 81 affects the capsule medical device 72 against the holding power. Then, the holding of the capsule medical device 72 is released, and the mounting portion 82 ejects the capsule medical device 72 forward with the fluid 73.

Note that the holding power of the mounting portion 82 is adjusted such that the ejection power is not so strong enough for the capsule medical device 72 to suddenly contact (hurtle against) the inner wall near the pharynx but is a predetermined power appropriate for the patient to easily swallow the capsule medical device 72.

The intraoral introduction portion 83 is thickly formed with the elastic member so as not to deform, and has a length capable of introducing the mounting portion 82 into an oral cavity 75. The length of the intraoral introduction portion 83 is adjusted to be longer than at least that of the inner portion of the oral cavity 75 so that the containing portion 81 is disposed outside the oral cavity 75 when the mounting portion 82 is inserted into near a pharynx 76. Note that the length of the oral cavity 75 is different depending on age and sex of a subject 74 and varies between individuals. Therefore, as the introduction-assisting instrument 71, there are a lineup of assisting instruments provided with the intraoral introduction portion 83 having a different length depending on the size thereof such as S, M, L, for example.

Accordingly, since the introduction-assisting instrument 71 is provided with the intraoral introduction portion 83, the containing portion 81 can be disposed outside the oral cavity 75, thus allowing the operation of crushing (compressing) the containing portion 81 to be easily performed. Furthermore, the introduction-assisting instrument 71 is capable of ejecting the capsule medical device 72 near the pharynx 76. Therefore, the ejection direction of the capsule medical device 72 is determined more precisely and unnecessary rotation is not applied to the capsule medical device 72.

Figure 14A:
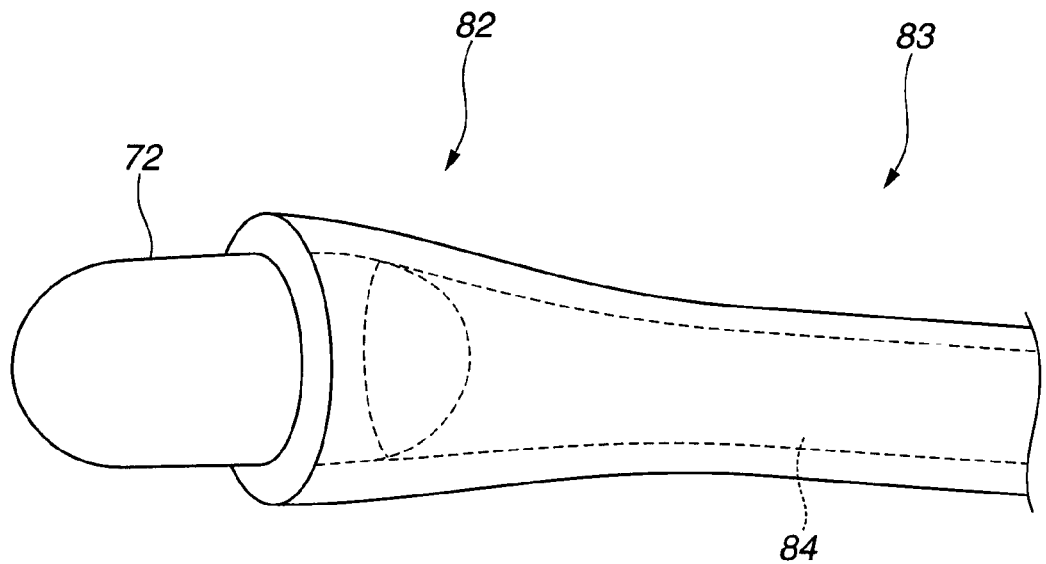
FIG. 14A is a view showing a vicinity of a mounting portion when a capsule medical device is mounted such that an observation direction of the device is opposite to an ejection direction thereof.

Note that, the introduction-assisting instrument 71 includes the containing portion 81, the mounting portion 82, and the intraoral introduction portion 83 which are integrally configured. Furthermore, in FIG. 13, the capsule medical device 72 is mounted to the mounting portion 82 such that the observation direction is oriented in the ejection direction. On the contrary, as shown in FIG. 14A, the capsule medical device 72 may be mounted to the mounting portion 82 such that the observation direction is reverse to the ejection direction.

Figure 14B:
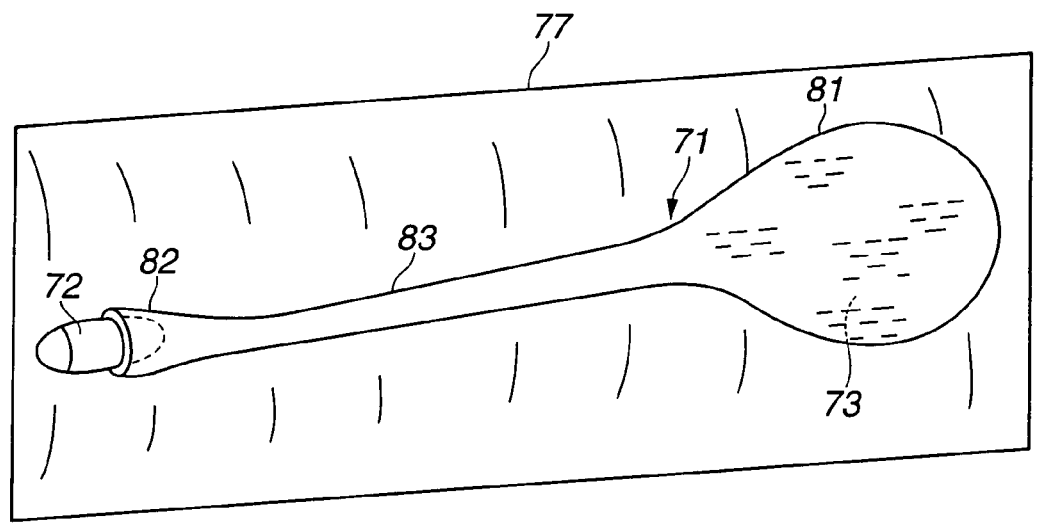
FIG. 14B is a view showing a situation in which an introduction-assisting instrument is sealed within a sterilized package before use.

The introduction-assisting instrument 71 configured as such is sealed within a package 77 in a sterilized state before use, as shown in FIG. 14B, after the fluid 73 is contained in the containing portion 81 and the capsule medical device 72 is detachably fitted thereto, for example.

In this case, as described above, the introduction-assisting instrument 71 is capable of fitting the capsule medical device 72 into the distal end portion of the mounting portion 82, so that the fitted capsule medical device 72 is held by the predetermined holding power and the fluid 73 contained in the containing portion 81 does not leak.

Then, when the capsule medical device 72 is used, the introduction-assisting instrument 71 is taken out of the package 77 to be used for a subject 74 in a lying state.

In a case of an example of prior art, in regions such as a desert or dense forest and at the time of disasters such as an earthquake or fire, it is sometimes difficult to secure clean water for swallowing the capsule medical device. However, with the introduction-assisting instrument 71 according to the present embodiment, the fluid 73 for swallowing the capsule medical device 72 is contained in advance in the containing portion 81, so that the capsule medical device 72 can be swallowed easily with the fluid 73 by crushing (compressing) the containing portion 81.

The introduction-assisting instrument 71 is introduced into near the pharynx 76 by inserting the mounting portion 82 to which the capsule medical device 72 is mounted into an oral cavity 75 of the subject 74 in a lying state. At this time, as for the introduction-assisting instrument 71, as described above, even if the mounting portion 82 is inserted into near the pharynx 76, the containing portion 81 is disposed outside the oral cavity 75, so that it is easy to operate the containing portion 81.

Then, the containing portion 81 of the introduction-assisting instrument 71 is crushed (compressed). At this time, by crushing (compressing) the rear end side of the containing portion 81 of the introduction-assisting instrument 71, the fluid 73 contained in the containing portion flows (moves) toward the mounting portion 82, and a predetermined power is generated in the direction to push forward and eject the capsule medical device 72 detachably mounted to the mounting portion 82.

Then, in the introduction-assisting instrument 71, the fluid 73 flows (moves) into the mounting portion 82 by the predetermined power from the containing portion 81 through the intraoral introduction portion 83. As described above, the introduction-assisting instrument 71 is configured such that the intraoral introduction portion 83 and the mounting portion 82 are thickly formed. Therefore, the intraoral introduction portion 83 and the mounting portion 82 do not deform.

Figure 15:
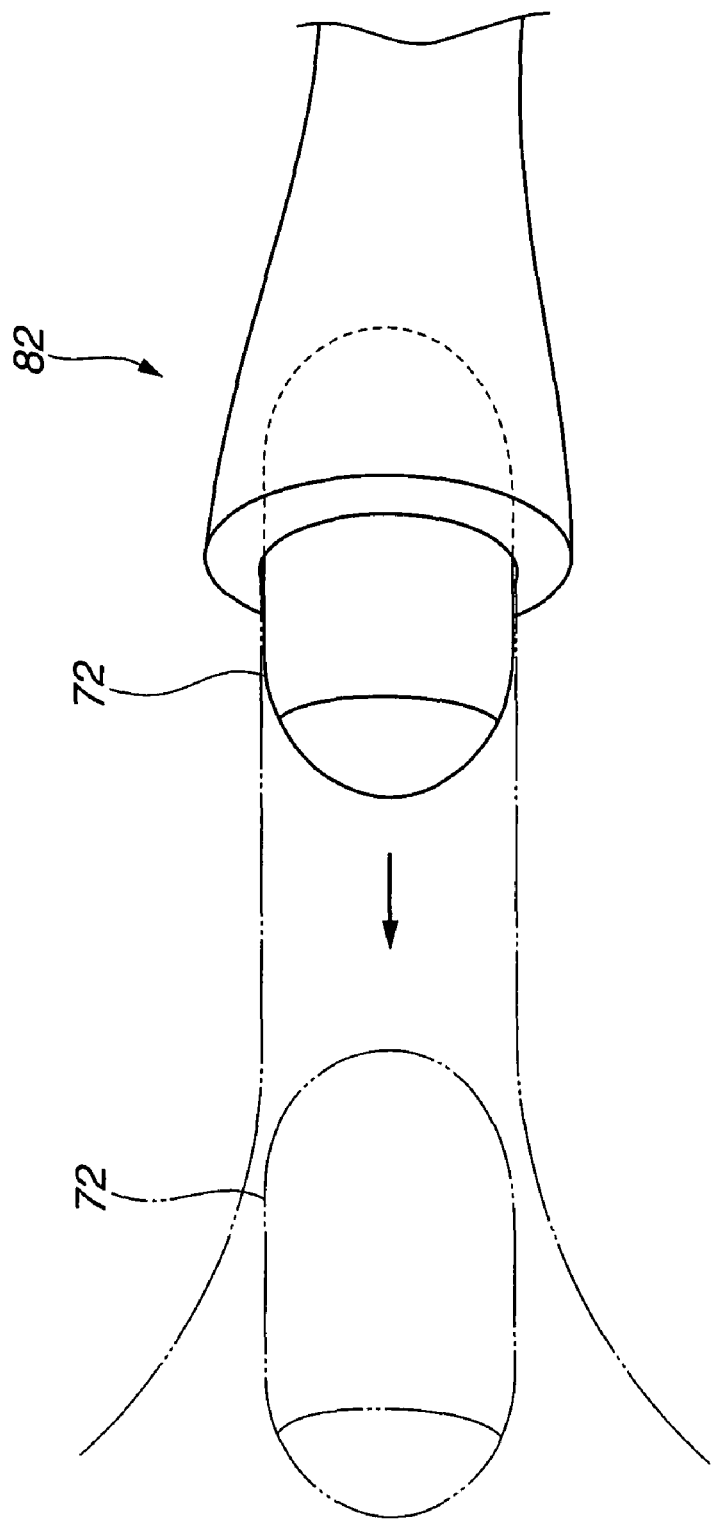
FIG. 15 is a descriptive view showing a vicinity of the mounting portion when a capsule medical device is ejected.

In the introduction-assisting instrument 71, the fluid 73 flows (moves) from the containing portion 81 into the mounting portion 82 to affect the capsule medical device 72 against the holding power of the mounting portion 82. Then, the holding of the capsule medical device 72 is released, and, as shown in FIG. 15, the introduction-assisting instrument 71 ejects forward the capsule medical device 72 with the fluid 73. At this time, the capsule medical device 72 is ejected near the pharynx 76, so that the ejection direction thereof is determined and unnecessary rotation is not applied.

The capsule medical device 72 passes through the tract in a body cavity by being swallowed from the oral cavity 75 of the subject 74 to obtain image data by optically picking up the inner wall surface of the tract in the body cavity, for example.

Since the subject 74 is in a lying state at this time, the capsule medical device 72 slowly passes through lumens in the body cavity such as esophagus and stomach by peristaltic motion, and it is possible to obtain a desired observation image, to sprinkle medication, and to perform therapeutic treatment and the like.

As a result, the introduction-assisting instrument 71 according to the present embodiment can secure the fluid 73 for swallowing the capsule medical device 72, and uniform the conditions for swallowing the capsule medical device 72 (amount of the fluid 73 and the like), thus obtaining an effect that the subject 74 can easily swallow the capsule medical device even in a lying state.

Figure 16:
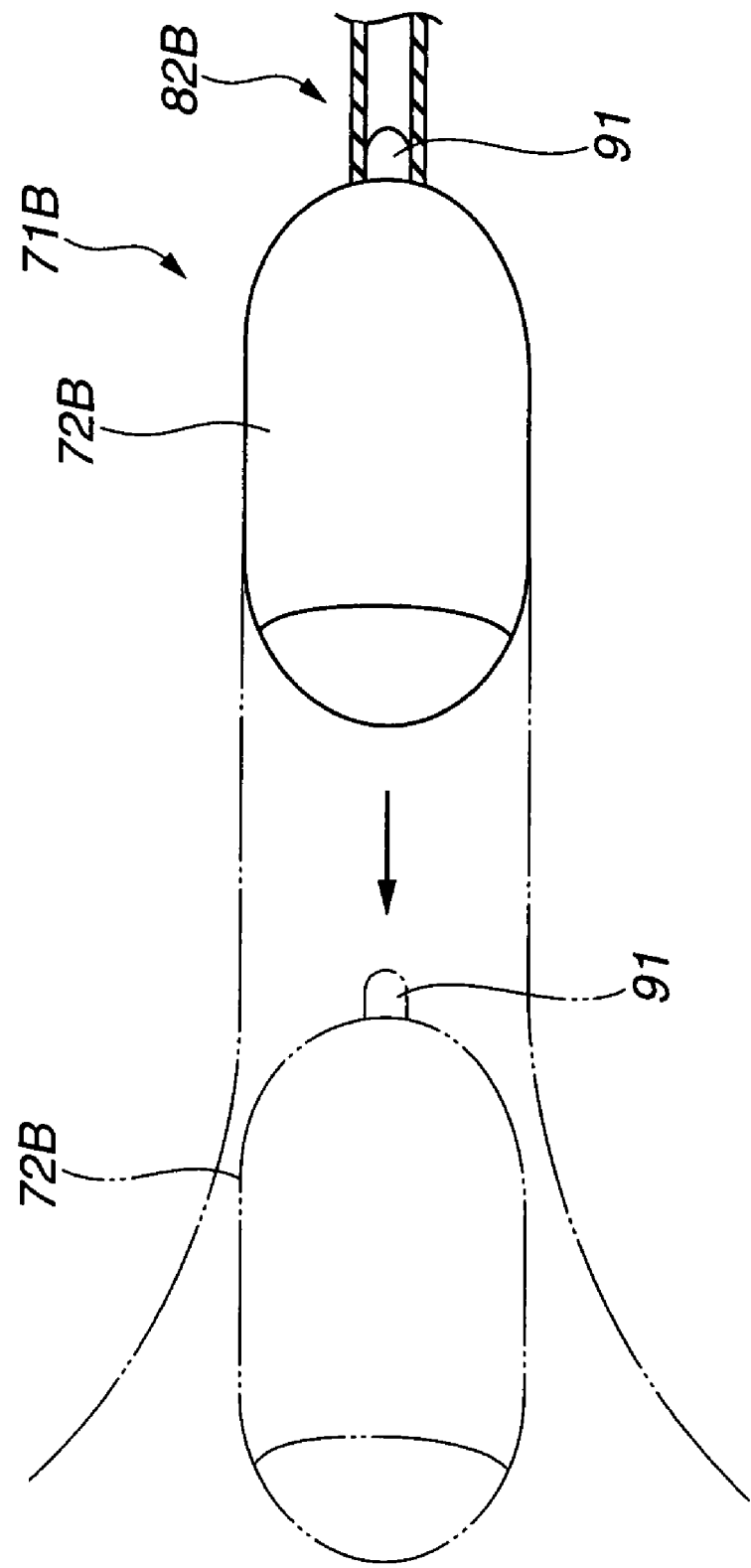
FIG. 16 is a descriptive view showing a vicinity of a mounting portion of an introduction-assisting instrument of a first modified example.

Note that the introduction-assisting instrument may include a mounting portion configured as shown in FIG. 16.

As shown in FIG. 16, the capsule medical device 72B is provided with a projection portion 91 at the rear end thereof. On the other hand, the introduction-assisting instrument 71B is provided with a mounting portion 82B having a small diameter into which the projection portion 91 of the capsule medical device 72B is fitted and held. According to this, the introduction-assisting instrument 71B has the mounting portion 82B into which only the projection portion 91 of the capsule medical device 72B is fitted, so that the ejection power is applied only to the projection 91 instead of the entire circumference of the capsule medical device 72B. Therefore the ejection power can be restrained.

Accordingly, the introduction-assisting instrument 71B fully prevents the capsule medical device 72B from suddenly contacting the inner wall of near the pharynx 76.

Figure 17:
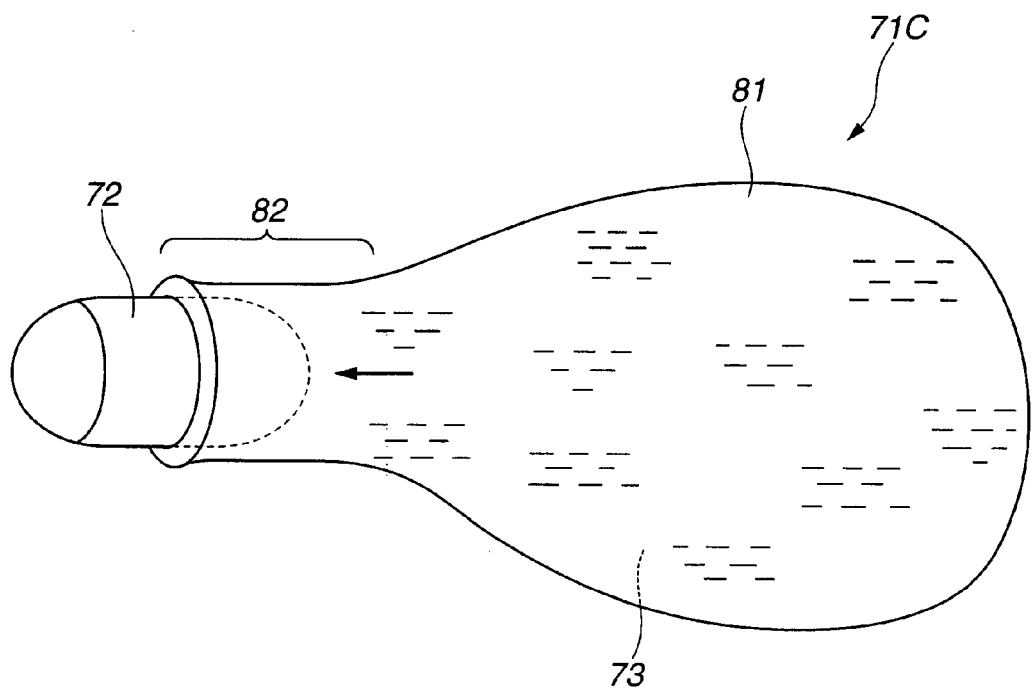
FIG. 17 is a view showing a configuration of an introduction-assisting instrument of a second modified example.

Note that the introduction-assisting instrument may be configured without the intraoral introduction portion, as shown in FIG. 17. The introduction-assisting instrument 71C shown in FIG. 17 includes a containing portion 81 and a mounting portion 82. The introduction-assisting instrument 71C has the containing portion 81 and the mounting portion 82 which are integrally configured.

Therefore, the introduction-assisting instrument 71C is configured to eject forward the capsule medical device 72 with the fluid 73 near the entrance of the oral cavity 75. Other configurations are almost the same as those of the above-described introduction-assisting instrument 71, so that a description thereof is omitted.

Seventh Embodiment

Figure 18:
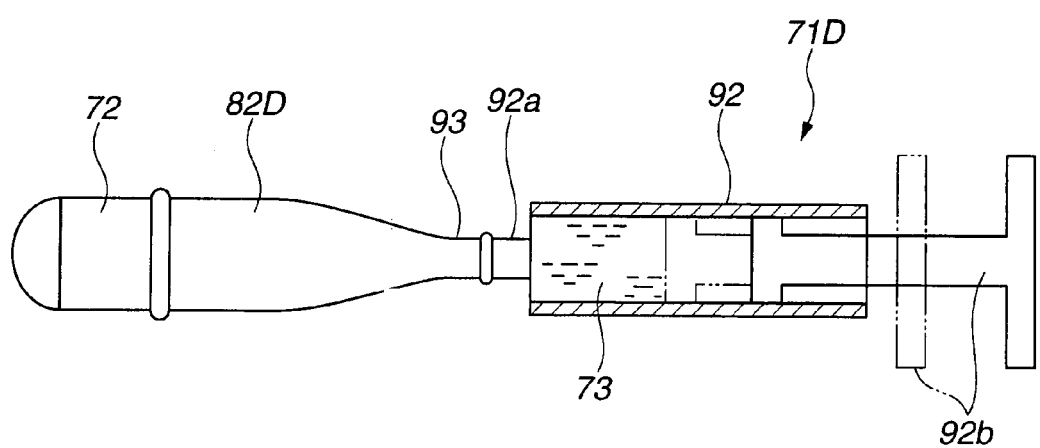
FIG. 18 is a view showing a configuration of an introduction-assisting instrument according to a seventh embodiment of the present invention.

FIG. 18 is a configuration view of the introduction-assisting instrument according to a seventh embodiment of the present invention.

In the above sixth embodiment, the containing portion 81, the mounting portion 82, and the intraoral introduction portion 83 are integrally configured. However, in the present embodiment, a containing portion is configured using a syringe. Since other configurations are the same as those according to the sixth embodiment, a description thereof is omitted, and the same components are designated by the same reference numerals.

That is, as shown in FIG. 18, an introduction-assisting instrument 71D according to the present embodiment includes a syringe 92 as a containing portion detachably attached to a rear end portion 93 of a mounting portion 82D.

The rear end portion 93 of the mounting portion 82D includes an opening connectable to a distal end side of the syringe 92, into which a distal end side small-diameter portion 92a of the syringe 92 can easily be fitted. The rear end portion holds the fitted distal end side small-diameter portion 92a of the syringe 92 and has a predetermined holding power to prevent a fluid 73 contained in the syringe 92 from leaking.

On the other hand, in the syringe 92, a knurl processing is carried out on the outer circumferential surface of the distal end side small-diameter portion 92a so as not to come off from the rear end portion 93 of the mounting portion 82D. The syringe 92, likewise with the containing portion 81 of the introduction-assisting instrument 71, can contain a predetermined amount of fluid 73, approximately 30 to 50 cc inside thereof.

The introduction-assisting instrument 71D according to the seventh embodiment configured as such is sealed within a package in a sterilized state, after the fluid 73 is contained in the syringe 92 and the mounting portion 82D into which the capsule medical device 72 is detachably fitted is connected to the distal end side small-diameter portion 92a of the syringe 92.

In using the capsule medical device 72, the introduction-assisting instrument 71D is taken out of the package to be used for a subject in a lying state.

The introduction-assisting instrument 71D is used such that the mounting portion 82D having the capsule medical device 72 mounted thereto is inserted into the oral cavity of the subject in a lying state. At this time, it is easy to operate the introduction-assisting instrument 71D, since the syringe 92 is disposed outside the oral cavity.

A piston 92b of the syringe 92 in the introduction-assisting instrument 71D is operated. Then, in the introduction-assisting instrument 71D, the fluid 73 contained inside the syringe 92 flows (moves) to the side of the mounting portion 82D, and a predetermined power is generated in a direction to push forward and eject the capsule medical device 72 detachably mounted to the mounting portion 82D.

With the introduction-assisting instrument 71D, the fluid 73 flows (moves) from the syringe 92 to the mounting portion 82D affects the capsule medical device 72 against the holding power of the mounting portion 82D. Then, the holding of the capsule medical device 72 is released and the introduction-assisting instrument 71D ejects forward the capsule medical device 72 with the fluid 73. After this, the operation of the capsule medical device 72 is the same as that according to the sixth embodiment.

According to this, the introduction-assisting instrument 71D has the same effects as those in the sixth embodiment.

Eighth Embodiment

Next, an eighth embodiment of the present invention will be described with reference to FIGS. 19 to 22B.

In the above-described sixth embodiment, the containing portion 81, the mounting portion 82, and the intraoral introduction portion 83 are integrally configured. However, in the present embodiment, a mounting portion is freely detachable from a containing portion. Since other configurations are the same as those according to the sixth embodiment, a description thereof is omitted, and the same components are designated by the same reference numerals.

Figure 19:
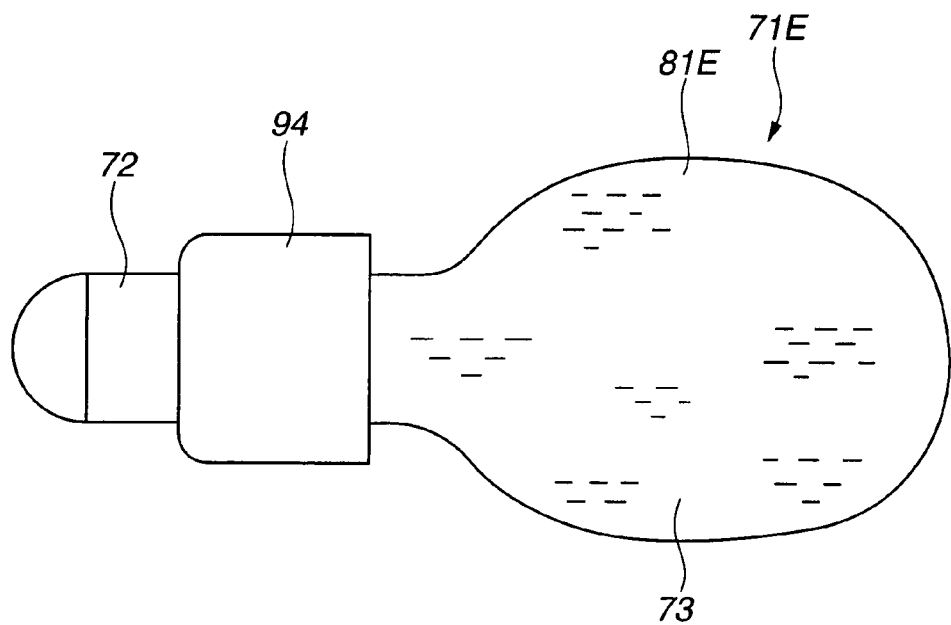
FIG. 19 is a side view showing a configuration of an introduction-assisting instrument according to an eighth embodiment of the present invention.

That is, as shown in FIG. 19, an introduction-assisting instrument 71E according to the present embodiment is provided with a joining member 94, as the mounting portion, which is freely detachable from a containing portion 81E.

Figure 20:
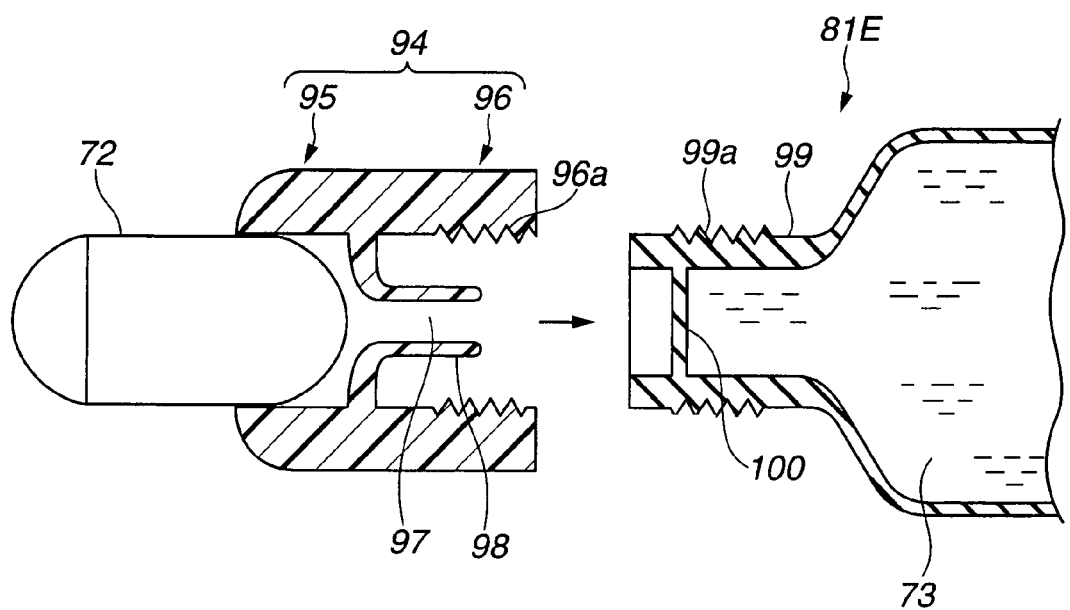
FIG. 20 is a cross-sectional view showing a configuration of a joining member and a containing portion of FIG. 19.

As shown in FIG. 20, the joining member 94 includes an attaching portion 95 to which the capsule medical device 72 is detachably attached, and a connection portion 96 freely detachable from the containing portion 81E. The connection portion 96 has a female screw portion 96a formed therein which is screwed to the containing portion 81E. The connection portion 96 includes a projection portion 98 for penetrating and punching a hole in (that is, perforating) a thin-walled portion described later of the containing portion 81E, for communicating with the containing portion, by a cylindrical portion forming a communication passage 97 inside the connection portion.

On the other hand, the containing portion 81E includes a male screw portion 99a, to which the female screw portion 96a of the joining member 94 is screwed, on an outer surface of a distal end side small-diameter portion 99, and a sealing portion made of a thin-walled portion 100 for containing and sealing the fluid 73 inside the containing portion 81E.

With the introduction-assisting instrument 71E, by screwing the female screw portion 96a of the joining member 94 to the male screw portion 99a of the containing portion 81E immediately before use, the joining member 94 is connected to the containing portion 81E, and the fluid 73 flows into the communication passage 97 as a result of the projection portion 98 of the joining member 94 perforating the thin-walled portion 100 of the containing portion 81E.

As for the introduction-assisting instrument 71E of the present embodiment configured as such, the containing portion 81E containing and sealing the fluid 73 and the joining member 94 to which the capsule medical device 72 is detachably mounted are individually contained in a package.

When the capsule medical device 72 is used, the whole introduction-assisting instrument 71E is taken out of the package by tearing the package and the like. Then the capsule medical device 72 is introduced into a body cavity of a subject in a lying state using the introduction-assisting instrument 71E.

Immediately before using the introduction-assisting instrument 71E, at first, the joining member 94 is connected to the containing portion 81E. Then, in the introduction-assisting instrument 71E, as described above, the projection portion 98 of the joining member 94 perforates the thin-walled portion 100 of the containing portion 81E, so that the fluid 73 flows into the communication passage 97 of the joining member 94.

Then, the introduction-assisting instrument 71D is used such that, in a state where the joining member 94 is connected to the containing portion 81E, the joining member 94 to which the capsule medical device 72 is mounted is introduced into the oral cavity of the subject in a lying state.

Figure 21:
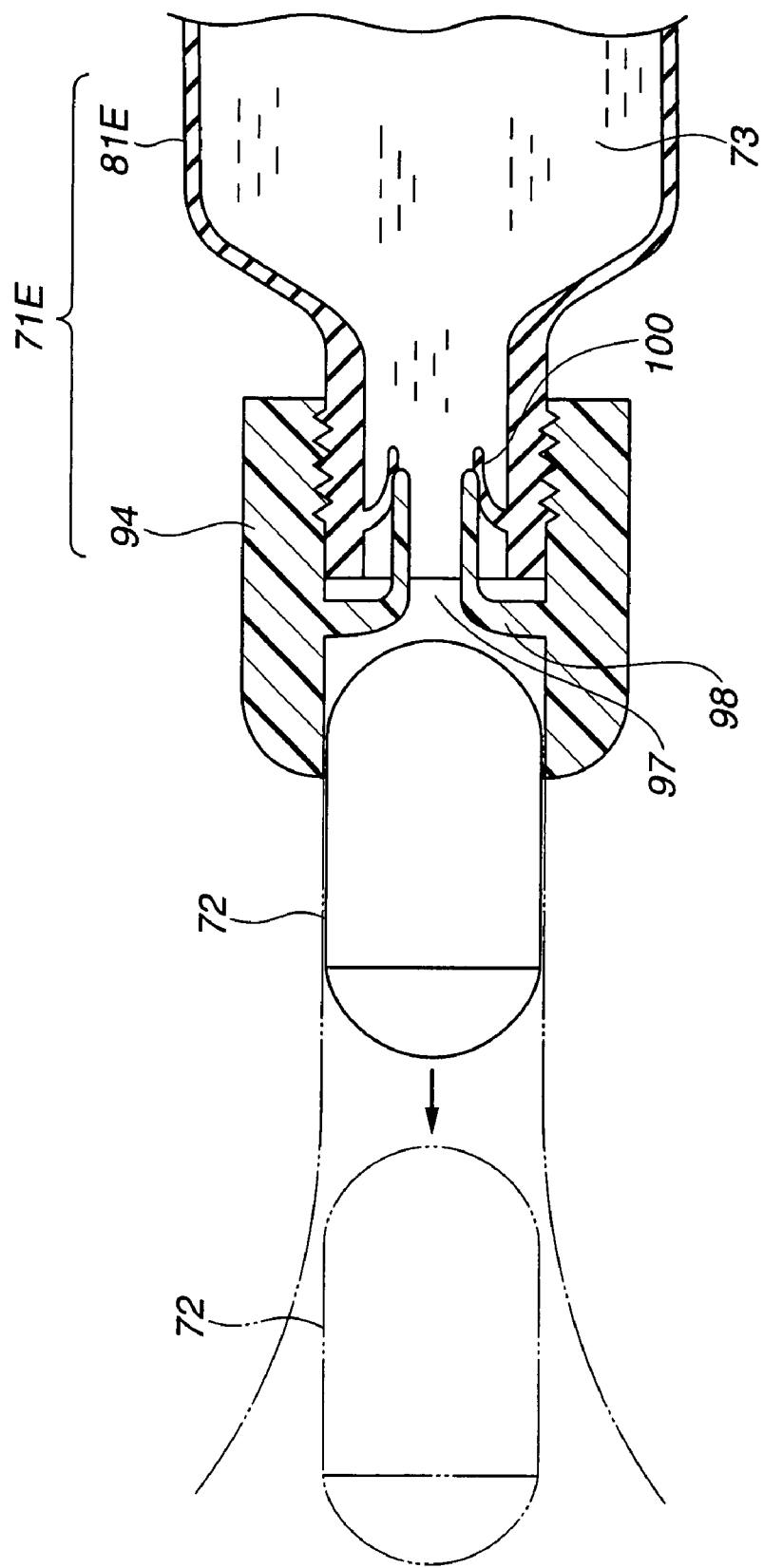
FIG. 21 is a descriptive view showing a situation in which the capsule medical device is ejected with the joining member in FIG. 20 being connected to the containing portion.

Then, as for the introduction-assisting instrument 71E, similarly as described in the sixth embodiment, the fluid 73 flows (moves) to the side of the joining member 94 by crushing (compressing) the rear end side of the containing portion 81E, and as shown in FIG. 21, the capsule medical device 72 detachably mounted to the joining member 94 is pushed forward and ejected. After this, the operation of the capsule medical device 72 is the same as that according to the sixth embodiment.

According to this, the introduction-assisting instrument 71E of the present embodiment can obtain the same effect as that of the sixth embodiment, and in addition, the fluid 73 does not change over time, since the fluid 73 is sealed until immediately before use.

Figure 22A:
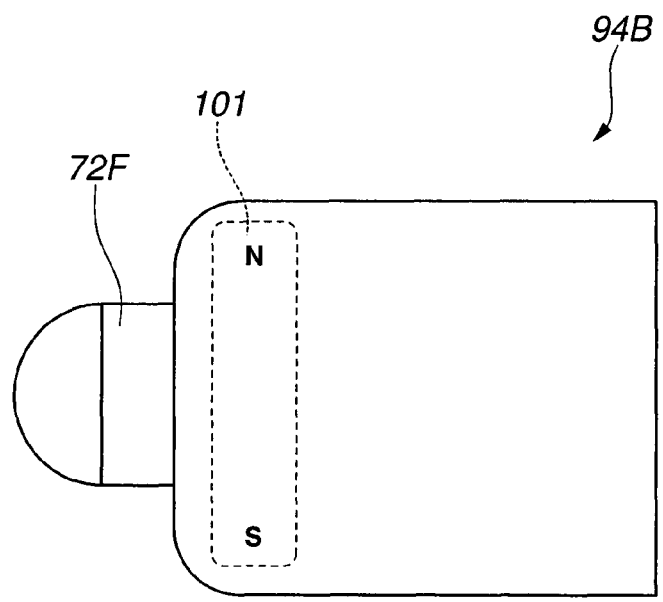
FIG. 22A is a side view showing a modified example of the joining member.
Figure 22B:
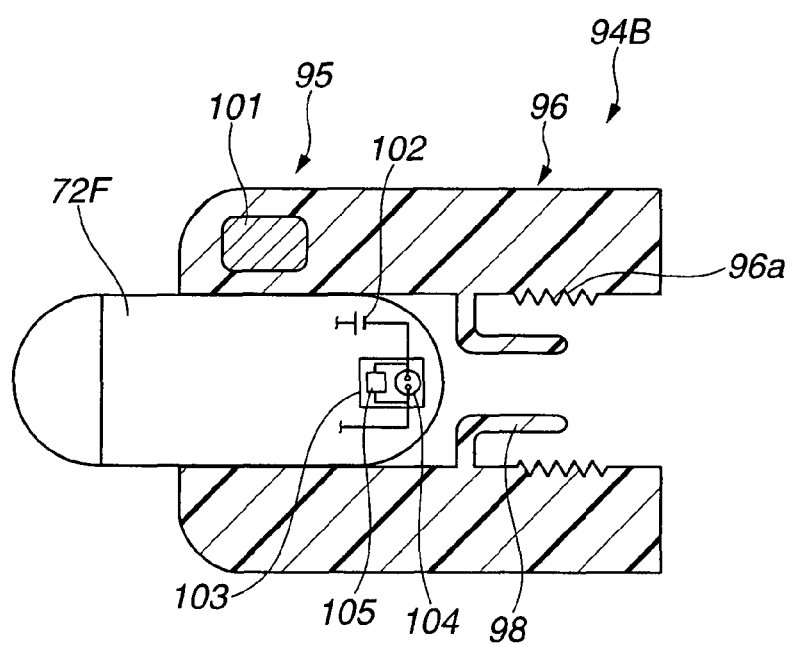
FIG. 22B is a cross-sectional view showing an internal structure of the joining member of FIG. 22A.

Note that the joining member may be configured as shown in FIGS. 22A and 22B.

As shown in FIGS. 22A and 22B, a joining member 94B incorporates a magnet 101 as a switch control means for restraining consumption of electric power in a capsule medical device 72F.

That is, as shown in FIG. 22B, an internal switch 103 for supplying/shutting off (ON/OFF) the electric power from a battery 102 to a load side such as the image pick-up element not shown and the like.

The internal switch 103 includes a reed switch 104 disposed at a position away from the magnet 101 in the capsule medical device 72F, at near rear end portion thereof for example, and an auxiliary switch 105 of which switch contact is disposed in parallel with that of the reed switch.

The reed switch 104 senses magnetism to be turned on from off-state. In addition, the auxiliary switch 105 is constituted by an electronic circuit. When the switch contact of the reed switch 104 is turned on, the auxiliary switch 105 becomes an operating state and turns on the switch contact in parallel with that of the reed switch 104. That is, once the reed switch 104 is turned on from off-state, then the electric power from the battery 102 is supplied to the load side by the auxiliary switch 105 even if the reed switch 104 is turned off.

With the joining member 94B configured in this way, the reed switch 104 crosses a portion to be affected by the magnetism by the magnet 101, that is a portion close to the magnet 101, when the capsule medical device 72F is ejected, so that the reed switch 104 is turned on from off-state at the time of crossing the portion. Since the electric power is supplied to the load side when the capsule medical device 72F is ejected, the consumption of battery 102 can be restrained before use.

Note that the present invention is not limited to the embodiments described above and various changes and modifications thereof, such as combination of each above-described embodiment, could be made without departing from the scope of the invention.

INDUSTRIAL APPLICABILITY

The use of the assisting table and the introduction-assisting apparatus allows a subject to easily swallow the capsule medical device, and thereby inspection and treatment in a body cavity can be smoothly performed.

The invention claimed is:

1. A medical system, comprising:
a capsule medical device used for performing a medical practice including inspection and treatment, the capsule medical device being introduced into a body cavity of a subject;
an introduction-assisting apparatus for capsule medical device for supporting the subject when the capsule medical device is introduced into the body cavity of the subject, wherein the introduction-assisting apparatus for capsule medical device includes:
a horizontally-holding device for generally horizontally holding an angle of an upper body of the subject except a cephalic part of the subject; and
an inclination-holding device for holding an angle of the cephalic part in an upwardly inclined state relative to the upper body; and
a string member attached to the capsule medical device by an adhesive wherein the attachment between the string member and the capsule medical device is released after a predetermined time period.

2. The medical system according to claim 1, wherein the introduction-assisting apparatus for capsule medical device further comprises a lateral position-holding device for holding the upper body of the subject in a lateral position.

3. The medical system according to claim 1, wherein the inclination-holding device is configured so that the inclination angle is adjustable.

4. The medical system according to claim 3, wherein the inclination-holding device is configured so that the inclination angle is adjustable by a pressing operation.

5. The medical system according to claim 3, wherein the inclination-holding device comprises:
a motor for adjusting the inclination angle; and
a switch for supplying drive current to the motor.

6. The medical system according to claim 1, wherein the inclination-holding device is detachably attached to the horizontally-holding device.

7. The medical system according to claim 1, wherein the adhesive is water-soluble.

8. The medical system according to claim 7, wherein
the capsule medical device includes an exterior member of a cylindrical shape having one end portion closed, an illumination device disposed inside of a transparent cover fixed to an opening of the other end portion of the exterior member, and an image-pickup element, and
the one end portion is attached with one end portion of the string member having a length corresponding to a distance from an oral cavity of the subject to a position immediately after passing through the throat, by gluing with the water-soluble adhesive.

* * * * *

UNITED STATES PATENT AND TRADEMARK OFFICE
CERTIFICATE OF CORRECTION

PATENT NO. : 8,091,164 B2
APPLICATION NO. : 11/661469
DATED : January 10, 2012
INVENTOR(S) : Hidetake Segawa et al.

It is certified that error appears in the above-identified patent and that said Letters Patent is hereby corrected as shown below:

On the Title Page

Item 30 Should Read:

(30)  Foreign Application Priority Data

Signed and Sealed this
Eleventh Day of June, 2013

Teresa Stanek Rea
*Acting Director of the United States Patent and Trademark Office*